(12) United States Patent
Peleg

(10) Patent No.: US 8,460,874 B2
(45) Date of Patent: Jun. 11, 2013

(54) USE OF RNA/DNA CHIMERIC PRIMERS FOR IMPROVED NUCLEIC ACID AMPLIFICATION REACTIONS

(75) Inventor: Ofer Peleg, Givatayim (IL)

(73) Assignee: Genaphora Ltd., Tel Aviv (IL)

( * ) Notice: Subject to any disclaimer, the term of this patent is extended or adjusted under 35 U.S.C. 154(b) by 711 days.

(21) Appl. No.: 12/667,261

(22) PCT Filed: Jul. 3, 2008

(86) PCT No.: PCT/IL2008/000918
§ 371 (c)(1),
(2), (4) Date: Jan. 4, 2010

(87) PCT Pub. No.: WO2009/004630
PCT Pub. Date: Jan. 8, 2009

(65) Prior Publication Data
US 2010/0291635 A1 Nov. 18, 2010

Related U.S. Application Data

(60) Provisional application No. 60/947,685, filed on Jul. 3, 2007.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC .............................................. 435/6.12, 91.2
See application file for complete search history.

(56) References Cited

U.S. PATENT DOCUMENTS

| 4,458,066 | A | 7/1984 | Caruthers et al. |
| 5,854,033 | A | 12/1998 | Lizardi |
| 6,001,611 | A | 12/1999 | Will |
| 6,103,476 | A * | 8/2000 | Tyagi et al. .................. 435/6.1 |
| 6,361,941 | B1 * | 3/2002 | Todd et al. .................. 435/6.14 |
| 6,492,121 | B2 * | 12/2002 | Kurane et al. ............... 435/6.18 |
| 6,794,142 | B2 | 9/2004 | Laird |
| 7,205,129 | B1 | 4/2007 | Dean |
| 2003/0175769 | A1 | 9/2003 | Heindl |

FOREIGN PATENT DOCUMENTS

| WO | 97/19193 A1 | 5/1997 |
| WO | 99/18241 A1 | 4/1999 |
| WO | 01/20035 A2 | 3/2001 |
| WO | 01/64952 A1 | 8/2001 |
| WO | 02/08408 A1 | 1/2002 |
| WO | 2006/112818 A1 | 10/2006 |

OTHER PUBLICATIONS

Miyachi et al., Anal. Chim. Acta 407, 1-10 (2000).*
Coljee et al., Nature Biotechnology 18, 789-791 (2000).*

(Continued)

*Primary Examiner* — Kenneth Horlick
(74) *Attorney, Agent, or Firm* — Rodney J. Fuller; Booth Udall Fuller, PLC

(57) ABSTRACT

Methods are provided for amplification of a nucleic acid sequence. The method use RNA/DNA chimeric oligonucleotides as primers. The primers have RNA residues scattered along their length and no two ribonucleotides in the prime are adjacent to one another. The methods are useful for reducing non-specific amplification products, such as primer dimers. The invention also provides kits comprising RNA/DNA chimeric oligonucleotide primers for practicing the amplification methods.

19 Claims, 10 Drawing Sheets

FORWARD PRIMER: 5'-GCATACTAAGCTGAGCGA

| |

REVERSE PRIMER: ATAACGA-CGATCGACTGA-5'

OTHER PUBLICATIONS

Cairns et al., Nucleic Acids Research 28(3), e9 i-vi (2000).*
Beaucage, S. L. et al., "Deoxynucleoside phosphoramidites—A new class of key intermediates for deoxypolynucleotide synthesis", Tetrahedron Lett., 22(20):1859-1862 (1981).
Birkenmeyer, Larry G. et al., "DNA probe amplification methods", J. Virological Methods, 35(2):117-126 (1991).
Chou, Quin et al., "Prevention of pre-PCR mis-priming and primer dimerization improves low-copy number amplifications", Nucleic Acids Res., 20(7):1717-1723 (1992).
Compton, J., "Nucleic acid sequence-based amplification", Nature, 350(6313):91-92 (1991).
Craxton, Molly, "Linear amplification sequencing, a powerful method for sequencing DNA", Methods: A companion to methods in enzymology, 3(1):20-26 (1991).
D'Aquila, Richard T. et al., "Maximizing sensitivity and specificity of PCR by preamplification heating", Nucleic Acids Res., 19(13):3749 (1991).
Don, R. H. et al., "'Touchdown' PCR to circumvent spurious priming during gene amplification", Nucleic Acids Res., 19(14):4008 (1991).
Ferrie, Richard M. et al., "Development, multiplexing, and application of ARMS tests for common mutations in the CFTR gene", Am. J. Hum. Genet., 51(2):251-262 (1992).
Landegren, Ulf, "Molecular mechanics of nucleic acid sequence amplification", Trends in Genetics, 9(6):199-202 (1993).
Lizardi, Paul M. et al., "Mutation detection and single-molecule counting using isothermal rolling-circle amplification", Nature Genetics, 19(3):225-232 (1998).
Nakano, Shu-Ichi et al., "Influences of Ribonucleotide on a Duplex Conformation and Its Thermal Stability: Study with the Chimeric RNA—DNA Strands", J. Am. Chem. Soc., 126(4):1088-1095 (2004).
Nelson, Norman C., "Rapid detection of genetic mutations using the chemiluminescent hybridization protection assay (HPA): overview and comparison with other methods", Crit. Rev. Clin. Lab. Sci., 35(5):369-414 (1998).
Rychlik, Wojciech, "Selection of primers for polymerase chain reaction", Mol. Biotechnol., 3(2):129-134 (1995).
Stump, Mark D. et al., "The use of modified primers to eliminate cycle sequencing artifacts", Nucleic Acids Research, 27(23):4642-4648 (1999).
Tyagi, Sanjay et al., "Multicolor molecular beacons for allele discrimination", Nat. Biotechnol., 16(1):49-53 (1998).
Tyagi, Sanjay et al. "Molecular Beacons: Probes that Fluoresce upon Hybridization", Nature Biotechnology, 14(3):303-308 (1996).
Walder Roxanne Y. et al., "Use of PCR primers containing a 3'-terminal ribose residue to prevent cross-contamination of amplified sequences", Nucleic Acids Research, 21(18):4339-4343 (1993).
Walker G. Terrance et al., "Strand displacement amplification-an isothermal, in vitro DNA amplification technique", Nucleic Acids Research, 20(7):1691-1696 (1992).
Walker G. Terrance et al., "Isothermal in vitro amplification of DNA by a restriction enzyme/DNA polymerase system", Proc. Natl. Acad. Sci. USA, 89:392-396 (1992).
TaqMan® PCR Reagent Kit with controls Protocol: Part No. 402823, Revision F, Applied Biosystems (Nov. 2007).

* cited by examiner

```
                            SEQUENCE LISTING

<160> NUMBER OF SEQ ID NOS: 15

<210> SEQ ID NO 1
<211> LENGTH: 57
<212> TYPE: DNA
<213> ORGANISM: Artificial Sequence
<220> FEATURE:
<223> OTHER INFORMATION: Synthetic Sequence

<400> SEQUENCE: 1
gcatactaag ctgagcgaca ttggccgtag ccatgcatgt attgctgcta gctgact        57

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
gcatactaag ctgagcga                                                   18

<210> SEQ ID NO 3
<211> LENGTH: 18
<212> TYPE: DNA
<213> ORGANISM: Artificial sequence
<220> FEATURE:
<223> OTHER INFORMATION: PCR primer

<400> SEQUENCE: 3
agtcagctag cagcaata                                                   18

<210> SEQ ID NO 4
<211> LENGTH: 22
<212> TYPE: DNA
<213> ORGANISM: Artificial sequence
<220> FEATURE:
<223> OTHER INFORMATION: PCR primer

<400> SEQUENCE: 4
tcgctattag atgagcctac gt                                              22

<210> SEQ ID NO 5
<211> LENGTH: 22
<212> TYPE: DNA
<213> ORGANISM: Artificial sequence
<220> FEATURE:
<223> OTHER INFORMATION: PCR primer

<400> SEQUENCE: 5
gagtctggac cgtatctcag tt                                              22
```

<210> SEQ ID NO 6
<211> LENGTH: 22
<212> TYPE: DNA
<213> ORGANISM: Artificial Sequence
<220> FEATURE:
<223> OTHER INFORMATION: PCR primer

<400> SEQUENCE: 6
tcgcuatuag atgagccuac gt                                              22

<210> SEQ ID NO 7
<211> LENGTH: 22
<212> TYPE: DNA
<213> ORGANISM: Artificial sequence
<220> FEATURE:
<223> OTHER INFORMATION: PCR primer

<400> SEQUENCE: 7
gagtctggac cguatctcag tt                                              22

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
gtcatcactg tgcctgcgta ct                                              22

<210> SEQ ID NO 9
<211> LENGTH: 22
<212> TYPE: DNA
<213> ORGANISM: Artificial Sequence
<220> FEATURE:
<223> OTHER INFORMATION: PCR primer

<400> SEQUENCE: 9
gcatgacgtt gagaccggca at                                              22

<210> SEQ ID NO 10
<211> LENGTH: 22
<212> TYPE: DNA
<213> ORGANISM: Artificial Sequence
<220> FEATURE:
<223> OTHER INFORMATION: PCR primer

<400> SEQUENCE: 10
gtcatcactg tgcctgcgua ct                                              22

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
gcatgacgtt gagaccggca at                                              22

<210> SEQ ID NO 12
<211> LENGTH: 21
<212> TYPE: DNA
<213> ORGANISM: Artificial Sequence
<220> FEATURE:
<223> OTHER INFORMATION: PCR primer

```
<400> SEQUENCE: 12
gcgcaagtac tctgtgtgga t                                              21

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
gtcgtactcc tgcttgctga t                                              21

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
gcgcaaguac tctgtgtgga t                                              21

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15
gtcguactcc tgcttgctga t                                              21
```

USE OF RNA/DNA CHIMERIC PRIMERS FOR IMPROVED NUCLEIC ACID AMPLIFICATION REACTIONS

RELATED APPLICATIONS

This application is the U.S. national stage of PCT/IL2008/000918, filed Jul. 3, 2008, which claims the benefit of U.S. provisional application No. 60/947,685, filed Jul. 3, 2007, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,970 byte ASCII (text) file named "Seq_List" created on Dec. 23, 2009.

FIELD OF THE INVENTION

The present invention relates to the field of amplification of nucleic acids. In particular, the present invention relates to the use of ribonucleotides in DNA primers and probes in reducing non-specific products in DNA-dependent DNA polymerase amplification reactions.

BACKGROUND OF THE INVENTION

In DNA-dependent-DNA-Polymerase amplification reactions such as. Polymerase Chain Reaction (PCR) and Real-Time quantitative PCR (qPCR), generation of non-specific amplification products may occur. Artifacts are derived from inappropriate hybridization products designated as primer dimers (Rychlik, 1995) and primer-probe dimers, resulting from weak interactions between primers or primers and probes such as TaqMan™ and molecular beacon probes. Undesired products form as a result of weak complementarity between the 3' ends of a primer to bases in non-target oligonucleotide strands in the reaction mix. This enables annealing of the primer to the non-target strand, followed by initiation and elongation of the non-specific dimer by the thermo stable DNA polymerase and leads to an efficient amplification of this undesired byproduct.

In real-time PCR this problem worsens due to appearance of non-specific byproducts that mask the detection of low concentrations of the target sequence after 30 cycles (Watson, 1989) in case of complementarity of at least one nucleotide at the 3' end, and after cycle 40 in case of no 3' complementarity at all. This problem is magnified in multiplex PCR amplification reactions and qPCR due to the presence of several primer sets and probes in the reaction mix, leading to deteriorated sensitivity and quality of the reaction. High Resolution Melt (HRM) analysis, which requires prior amplification of the target sequence to high copy number, is especially sensitive to the purity of the sample. The presence of post-amplification artifacts such as primer dimers or non-specific byproducts can make HRM results difficult to interpret.

Ferrie et al. (1992) showed that under cold-start conditions, every possible combination of two different primers in a multiplex reaction would generate primer-dimers, irrespective of any primer complementarity.

Non-specific amplification products can be reduced by careful primer design, use of stringent PCR protocols (Don et. al., 1991) and use of 'hot-start' enzymes (Chou et al., 1992; D'Aquila et al., 1991; TaqMan™ PCR Reagent Kit Protocol, P. E. Applied Biosystems). However, hot-start enzymes do "leak" and apparently there are no absolute hot-start enzymes.

Several methods for the reduction of non-specific amplification products in PCR have been described: US Patent Application 2003/0175769 discloses the use of poly-hydroxy-aryl-poly-acid with 3-6 ortho-hydroxy acid moieties as an additive to a nucleic acid amplification reaction that can result in prevention of primer dimer formation. European Patent Application EP 0866071 and PCT Application WO 2006/112818 disclose the use of covalently modified nucleotides at or near the 3' end of the primer for reduction of non-specific amplification products, in particular primer dimers.

European Patent Application EP 1201768 discloses methods and reagents to reduce non specific amplification involving the use of oligonucleotide primers in which at least one of the 3 nucleotides at the 3' end of the primer is a modified nucleotide selected from the group consisting of 2'-O-amino-methyl-nucleotides, 2'-amino-methyl-nucleotides, 2'-fluoro-nucleotides, and arabinose nucleotides.

U.S. Pat. No. 7,205,129 and PCT Application WO 01/64952 disclose the use of a method for the reduction of artifacts during nucleic acids amplification based on the use of template-deficient oligonucleotides as primers. These template-deficient oligonucleotides comprise template-deficient nucleotides, preferably at or near the 5' end. These template-deficient nucleotides, which may be modified nucleotides, derivatized nucleotides, nucleotide analogs or ribonucleotides, cannot serve as templates for nucleic acid synthesis, i.e., they prevent the synthesis of a nucleic acid strand complementary to a nucleic acid strand containing a template-deficient nucleotide at or beyond the site of the template-deficient nucleotide. In other words, the template-deficient oligonucleotide primers disclosed in U.S. Pat. No. 7,205,129 and WO 01/64952 cannot be fully replicated. U.S. Pat. No. 7,205,129 and WO 01/64952 teach away from the present invention by blocking DNA elongation at or beyond the site of a template-deficient nucleotide.

The standard situation where the primers do not undergo any modification delimits the detection sensitivity of assays that rely on DNA dependent DNA polymerase amplification, such as qPCR and HRM. The appearance of amplification products after cycle 30 is defined as a "twilight zone". The detection is questionable and further examinations such as Tm (melting temperature) analysis and sequencing of the product are necessary.

Blocking the formation of non-specific template-independent products will prevent primer inactivation and diversion of the reaction towards the formation of non-informative byproducts. Elimination or any postponement in the appearance of non-specific template-independent products in DNA-dependent DNA-polymerase amplification reactions should increase the reaction robustness, specificity and sensitivity.

The existing methods for eliminating or reducing artifacts in nucleic acid amplification reactions involve chemical modifications or insertion of stretches (above 2 bases in a row) of RNA bases into primers, that require specific enzymatic or other, complicated, chemical reactions, or modifying nucleotides at the 5' end of the primers in order to allow sufficient priming.

Thus, there is an unmet need for simpler, more effective, and more economical methods for improved nucleic acid amplification reactions and especially for real-time PCR and high resolution melt analysis applications with improved specificity and sensitivity.

SUMMARY OF THE INVENTION

The present invention provides methods for the reduction or elimination of non-specific amplification products and other artifacts produced by in-vitro DNA-dependent-DNA-Polymerase amplification reactions applications such as, but not limited to, Polymerase Chain Reaction (PCR), real time quantitative PCR (qPCR), and High Resolution Melt (HRM) analysis. More specifically, the present invention provides materials, kits and methods for designing and using RNA/DNA chimeric primers and probes for reducing or eliminating non-specific amplification products in DNA-dependent-DNA polymerase amplification reactions.

The present invention reduces the formation of non-specific template independent byproducts by embedding ribonucleotides in the DNA sequence of primers and probes in a non-random manner, scattered along the length of the primer or probe, preferably not at the 5' end, while avoiding RNA stretches. The method of the present invention impedes the initiation of DNA synthesis from sites where RNA modification occurs, but allows the elongation of DNA beyond the site of RNA modification of the primer.

It has now been found that, surprisingly, incorporating only a few ribonucleotides in a DNA primer and/or probe (i.e. an RNA/DNA chimeric molecule) can have a beneficial impact on reducing generation of undesired artifacts produced by in-vitro DNA-dependent DNA-polymerase amplification reactions, provided that the ribonucleotides are non-adjacent. Embedding only a few RNA bases into DNA-primers and/or probes is simple and does not require any special enzymatic addition or chemical manipulations.

Without wishing to be bound by any particular theory or mechanism of action, the invention is based in part on the finding that the presence of RNA bases in the template strand in proximity to the initiation zone strongly reduces the efficiency of initiation of DNA synthesis, whereas DNA elongation of the primer strand is less strongly affected by RNA bases embedded in the template strand, provided that the RNA bases are non-adjacent. In the context of the present invention the initiation zone is defined as the point where DNA synthesis starts on the primer-template duplex.

It is now disclosed that embedding RNA bases in pre-designed locations in DNA primers and probes significantly decreases the formation of non-specific amplification products in DNA-dependent DNA amplification reactions. Under standard amplification reaction conditions (i.e., when the primers and probes contain only DNA), primers and probes may provide a functional initiation zone for an undesired non-specific reaction resulting in primer amplification, in addition to the amplification of a desired target sequence, due to the large excess of primers in the reaction mixture. In contrast, the RNA/DNA chimeric primers and probes of the present invention are designed to provide a non-functional initiation zone when forming non-specific duplexes, thereby leaving the RNA/DNA chimera-target template duplex as the only available initiation zone in the reaction mixture. However, since elongation of DNA is possible even when a few ribonucleotides are embedded in the template, provided no RNA stretches are present as in the RNA/DNA chimeric primers of the present invention, amplification of the target sequence will proceed, albeit with somewhat reduced efficiency.

The present invention accordingly provides methods useful for the reduction or elimination of non-specific template independent products in DNA-dependent-DNA-polymerase amplification by using RNA/DNA chimeric oligonucleotide primers, thus increasing specificity and sensitivity of target sequence detection and quantification by PCR. According to alternative embodiments, the amplification is performed using RNA/DNA chimeric oligonucleotide primers and probes.

The present invention also provides kits useful for the reduction or elimination of non-specific template independent products in DNA-dependent-DNA-polymerase amplification reactions, comprising RNA/DNA chimeric primers and necessary chemical ingredients and enzymes for use in DNA-dependent-DNA-polymerase amplification reactions. According to alternative embodiments, the amplification is performed using RNA/DNA chimeric oligonucleotide primers and probes.

In one aspect the present invention provides a method of reducing or eliminating formation of artifacts and non-specific amplification products in a DNA-dependent DNA polymerase amplification reaction. The method comprises using at least one RNA/DNA chimeric oligonucleotide as a forward or as a reverse primer and a DNA-dependent DNA polymerase to amplify a target sequence, and optionally one or more oligonucleotide probe, wherein the chimeric oligonucleotide comprises at least one ribonucleotide; and wherein the number of ribonucleotides located at or within 10 nucleotides of the 3' end of the chimeric oligonucleotide will allow the initiation of DNA synthesis and will not prevent DNA elongation when the primer forms a duplex with the intended target sequence and will impede initiation of DNA synthesis from primer-primer dimers or primer-probe dimers; and wherein no two ribonucleotides in the primer are adjacent to one another.

In some embodiments, the forward primer and the reverse primer are both RNA/DNA chimeric oligonucleotides.

In some embodiments, all the primers and probes used in the amplification reaction have an identical base as the 3' terminal base. In preferred embodiments, the identical 3' terminal base of the chimeric oligonucleotides is selected from A or T. In certain embodiments, a base which is "complementary" to said base at the 3' end of at least one chimeric primer, or a base adjacent to said "complementary" base, is a ribonucleotide. By way of example, if the terminal base is a T, each A in the primer may be replaced by a ribonucleotide, or a ribonucleotide may be placed adjacent to each A in the primer in order to impede initiation of amplification of any hypothetical primer-primer dimer that might form.

In various embodiments, each chimeric primer or probe comprises at least one ribonucleotide located at or within one to 5 nucleotides upstream or downstream of at least one of the nucleotides that is complementary to its own 3' end or the 3' end of another primer or probe in the reaction mixture. In preferred embodiments, each chimeric primer or probe comprises a ribonucleotide located at or adjacent to at least one of the nucleotides that is complementary to its own 3' end or the 3' end of another primer or probe in the reaction mixture.

The methods of the present invention can be used in any DNA-dependent DNA polymerase amplification reaction and amplification product detection method. In some embodiments the DNA-dependent DNA polymerase amplification is selected from the group consisting of exponential rolling circle amplification (ERCA), rolling circle amplification (RCA), multiple displacement amplification (MDA), strand displacement amplification (SDA), nucleic acid sequence based amplification (NASBA), transcription-mediated amplification (TMA), polymerase chain reaction (PCR), real-time quantitative PCR (qPCR), self-sustained sequence replication (3SR), amplification with $Q\beta$ replicase, and cycle sequencing. In preferred embodiments the DNA-dependent DNA polymerase amplification is real-time quantitative PCR (qPCR).

In another aspect the present invention provides a kit for carrying out DNA-dependent DNA polymerase amplification reactions. The kit utilizes the methods and materials described above and is useful for reducing or eliminating non-specific amplification products in a DNA-dependent DNA polymerase amplification reaction.

In some embodiments the kit comprises: (i) at least one RNA/DNA chimeric oligonucleotide as a forward or as a reverse primer, and optionally one or more oligonucleotide probe wherein the chimeric oligonucleotide comprises at least one ribonucleotide, wherein the number and composition of ribonucleotides located at or within 10 nucleotides of the 3' end of the chimeric oligonucleotide will allow the initiation of DNA synthesis and will not prevent DNA elongation when the primer forms a duplex with the intended target sequence and will impede initiation of DNA synthesis from primer-primer dimers or primer-probe dimers, and wherein no two ribonucleotides in the primer are adjacent to one another; (ii) a DNA-dependent DNA polymerase; and (iii) the necessary reagents and buffers to carry out the amplification reaction.

In some embodiments, the forward primer and the reverse primer are both RNA/DNA chimeric oligonucleotides.

In some embodiments, all the primers and probes in the kit have an identical base as the 3' terminal base. In preferred embodiments, the identical 3' terminal base of the chimeric oligonucleotides is selected from A or T. In certain embodiments, a base which is "complementary" to said base at the 3' end of at least one chimeric primer, or a base adjacent to said "complementary" base, is a ribonucleotide.

In various embodiments, each chimeric primer or probe comprises at least one ribonucleotide located at or within one to 5 nucleotides upstream or downstream of at least one of the nucleotides that is complementary to its own 3' end or the 3' end of another primer or probe in the kit. In preferred embodiments, each chimeric primer or probe comprises a ribonucleotide located at or adjacent to at least one of the nucleotides that is complementary to its own 3' end or the 3' end of another primer or probe in the kit.

The kit can be used to perform any kind of DNA-dependent DNA polymerase amplification reaction. According to various embodiments, the DNA-dependent DNA polymerase amplification is selected from the group consisting of exponential rolling circle amplification (ERCA), rolling circle amplification (RCA), multiple displacement amplification (MDA), strand displacement amplification (SDA), nucleic acid sequence based amplification (NASBA), transcription-mediated amplification (TMA), polymerase chain reaction (PCR), real-time quantitative PCR (qPCR), self-sustained sequence replication (3SR), amplification with Qβ replicase, and cycle sequencing.

In some embodiments, the kit further comprises the means to detect nucleic acid amplification products, for example, a detectable label, a fluorogenic probe, or a minor groove binder fluorescent dye.

The present invention will be more fully understood from the following detailed description and examples that follow.

DETAILED DESCRIPTION OF THE INVENTION

Figure 1:
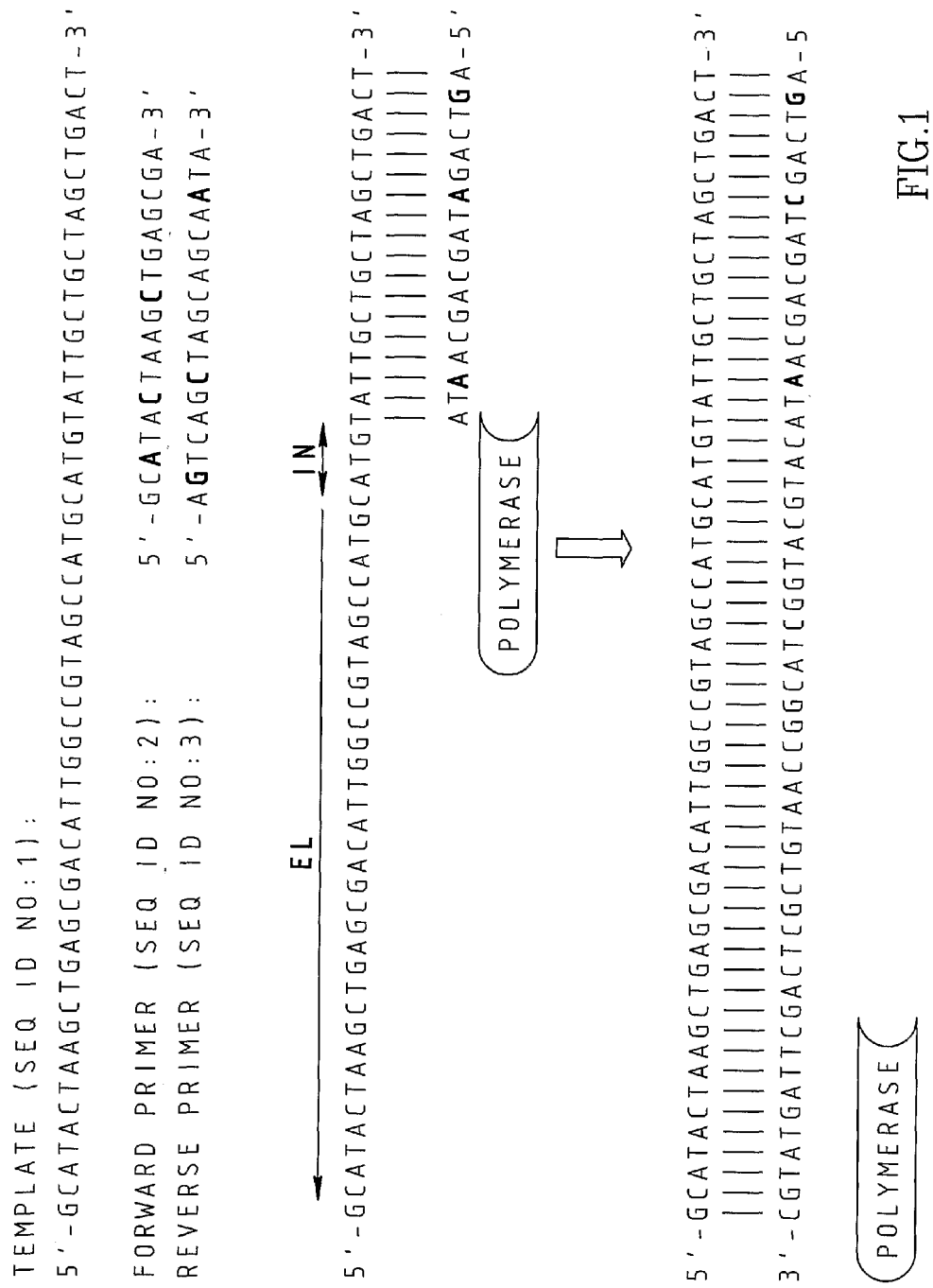
FIG. 1 is a diagram showing how the first cycle of a template dependent amplification using RNA/DNA chimeric primers proceeds. The initiation zone (IN) and the elongation zone (EL) are free of embedded RNA bases. The template sequence (SEQ ID NO:1) is a hypothetical sequence and has no significant similarity to sequences in the NCBI nucleotide database. RNA bases are bolded.

The present invention provides methods and kits useful for reducing or eliminating non-specific amplification products and other artifacts generated during in-vitro DNA-dependent-DNA polymerase amplification reactions. The methods utilize RNA/DNA chimeric oligonucleotide primers, and optionally, RNA/DNA chimeric oligonucleotide probes. They are simple and inexpensive and are applicable to any DNA-dependent-DNA polymerase amplification method.

DEFINITIONS

To aid in the understanding of the invention, several terms are defined below.

As used herein, a "primer dimer" or "primer-probe dimer" is a double stranded template-independent artifact of an amplification reaction whose length is typically close to the sum of the two primer lengths or the primer and probe length, minus the overlapping zone.

The terms "probe", "molecular beacon probe", "TaqMan probe", and "dual-labeled probe" indicate a nucleic acid probe that hybridizes with a specific nucleic acid. In the case of molecular beacons the probe is a hairpin-shaped sequence with a central stretch of nucleotides complementary to the target sequence and its termini comprising short mutually complementary sequences, one terminus covalently bound to a fluorophore (reporter dye) and the other to a quenching dye. In the native state, the termini are hybridized and the reporter and quencher dye are in sufficiently close proximity that fluorescence from the reporter dye is effectively quenched by the quencher dye. Hybridized probe, in contrast, results in a linearized conformation in which the extent of quenching is decreased. In the case of a TaqMan probe or dual-labeled probe the probe is not necessarily hairpin shaped, and the reaction should contain a 5'->3' hydrolysis enzyme that hydrolyzes the 5' labeled base thereby separating the probe from the quencher. Thus, by monitoring emission changes for the fluorescence dyes, it is possible to indirectly monitor the formation of amplification product (see, for example, Tyagi, S, and Kramer, F. R., Nature Biotechnology 14:303-308 (1996); and Tyagi, S. et al., Nat. Biotechnol. 16:49-53 (1998)). Thus, as the reaction proceeds, and the quantity of the amplified products increases, the fluorescence increases as well. An amplification plot is depicted that represents the change in fluorescence as a function of cycle number, in which an arbitrary threshold is set, usually at 10 standard deviations above the mean of base line emission calculated from the initial cycles. Once the threshold is chosen, the point at which the amplification plot crosses the threshold is defined as the threshold cycle (C(t)) or crossing point (CP). The threshold cycle is predictive of the quantity of the sequence.

The term "dsDNA binding dye" or "non-specific probe" indicates a chemical component that does not interact with single-stranded DNA but actively intercalates with double-stranded DNA and emits light upon excitation in this state. Examples of fluorescent dyes include, but are not limited to, SYBR Green I, SYTO 9, LC Green, Eva Green, and others.

As used herein, the term "nucleotide" refers to either a deoxyribonucleotide (containing 2-deoxy-D-ribose) or a ribonucleotide (containing D-ribose). The terms "ribonucleotide" and "RNA base", and the terms "deoxyribonucleotide" and "DNA base" are used interchangeably.

The term "oligonucleotide" is defined as a molecule comprised of two or more deoxyribonucleotides and/or ribonucleotides, preferably more than six. Its exact size will depend upon many factors, which, in turn, depend upon the ultimate function and use of the oligonucleotide.

The term "primer" as used herein refers to an oligonucleotide, which is capable of acting as a point of initiation of oligonucleotide synthesis of a primer extension product, complementary to a nucleic acid strand, which serves as a template. Primer extension is initiated in the presence of nucleotides and an inducing agent such as a DNA polymerase and at a suitable temperature and pH.

The terms "target", and "target sequence" refer to a region or sequence of a nucleic acid, which is to be amplified. The terms "non-specific amplification" and "template-independent amplification" as used herein are used interchangeably and refer to the amplification of nucleic acid sequences other than the target sequence, which results from primers hybridizing to sequences other than the target sequence and then serving as a substrate for primer extension.

The terms "RNA/DNA chimera", and "RNA/DNA chimeric oligonucleotide", are used interchangeably and defined as an oligonucleotide which comprises deoxyribonucleotides and at least one ribonucleotide, which can function as primer or probe in a nucleic acid amplification reaction.

As used herein, the term "initiation zone" refers to the zone where initiation of DNA synthesis of primer elongation products takes place. It includes the point where DNA synthesis starts and extends for a few nucleotides in the direction of DNA synthesis.

The terms "upstream" and "downstream" are used herein to define the location of a nucleotide in relation to another nucleotide within the sequence of an oligonucleotide. A nucleotide located upstream of another nucleotide means that the first nucleotide is located 5' to the other nucleotide. A nucleotide located downstream of another nucleotide means that the first nucleotide is located 3' to the other nucleotide.

DESCRIPTION OF PREFERRED EMBODIMENTS

It has been discovered that non-specific amplification products could be reduced or even eliminated by the use of RNA/DNA chimera primers. In the disclosed methods, such non-specific amplification artifacts contain RNA in the initiation zone and are poorly amplified. The presence of ribonucleotides in selected locations in oligonucleotide primers and probes increases the sensitivity of real-time PCR assays, due to reduction or even elimination of non-specific amplification products. The selection process is not random and may require careful design to obtain optimal results. Generally speaking, the RNA bases can be scattered along the primer from the 3' end to the last 5' base. Since primer dimers are the most prevalent artifact, the most important candidate bases for RNA embedding are located around the middle of the primer. The 5' end of the primer is the least important base in the modification list. In the design of the chimera, it is preferable to prevent strings of RNA that could block the elongation of DNA.

Without wishing to be bound by any theory or mechanism of action, it seems that non-specific amplification products are generated mainly when base-pairing occurs between the 3' end of a primer and a complementary base on another primer or probe, or even when self-pairing occurs between the 3' end of a primer and a complementary base on the same primer.

Thus, in a DNA-dependent DNA polymerase amplification reaction, if a ribonucleotide is present in close proximity to a base complementary to the 3' end of another primer or probe or to its own 3' end, primer-dimer or primer-probe dimer elongation will be hampered due to the presence of the ribonucleotide in the initiation zone and generation of non-specific amplification products will be reduced or even eliminated.

The present invention accordingly provides a method of reducing or eliminating non-specific amplification products in a DNA-dependent DNA polymerase amplification reaction comprising conducting a nucleic acid amplification reaction using at least one RNA/DNA chimeric oligonucleotide as a forward or as a reverse primer and a DNA-dependent DNA polymerase to amplify a target sequence, and optionally one or more oligonucleotide probe, wherein the chimeric oligonucleotide comprises at least one ribonucleotide; and wherein the number of ribonucleotides at or within 10 nucleotides of the 3' end of the chimeric oligonucleotide will allow the initiation of DNA synthesis and will not prevent DNA elongation when the primer forms a duplex with the intended target sequence and will impede initiation of DNA synthesis from primer-primer dimers or primer-probe dimers; and wherein no two ribonucleotides are adjacent to one another in the primer.

A better efficiency in reduction of non-specific amplification products is obtained when the forward primer and the reverse primer are both RNA/DNA chimeras. In some embodiments, all primers and probes used in the amplification reaction have the same base at the 3' end. It is desirable that all primers have the same 3' end in order to minimize the number of bases to be modified. In a preferred embodiment the 3' end of all primers used in the amplification reaction is either A or T.

In some embodiments at least one chimeric primer or probe comprises a ribonucleotide located at or adjacent to at least one of the nucleotides that is complementary to its own 3' end or the 3' end of another primer or probe in the reaction mixture.

In various embodiments, each chimeric primer or probe comprises at least one ribonucleotide located at or within one to 5 nucleotides of at least one of the nucleotides that is complementary to its own 3' end or the 3' end of another primer or probe in the reaction mixture. In preferred embodiments, each chimeric primer or probe comprises a ribonucleotide located at or adjacent to at least one of the nucleotides that is complementary to its own 3' end or the 3' end of another primer or probe in the reaction mixture.

Numerous configurations, in terms of the placement of the RNA bases, can be used in the RNA/DNA chimera disclosed in the present invention, ranging from modification of any one of the nucleotides complementary to its own or to the other primer(s) 3' end, or modification of its neighbor(s), to modification of all such nucleotides, provided no RNA stretches occur in the modified oligonucleotide. It is however not necessary to modify all nucleotides complementary to the 3' end of itself and other primer(s) or the neighbor(s) of all such nucleotides, since regions crowded with RNA might occur and block elongation.

The RNA bases can be scattered along the primer from the 3' end to the last 5' base. Since primer dimers are the most prevalent artifact, the most important bases to modify are located around the middle of the primer. The 5' end of the primer is the least important base in the modification list. In the design of the chimera, it is preferable to prevent strings of RNA that could block the elongation of DNA.

The design and use of amplification primers in general is well known in the art. The primers of the present invention are distinguished by the inclusion of RNA bases in the primer sequence. Other aspects of the primer, such as the overall length and sequence, are selected following the standard practice of primer design. One with skill in the art will recognize that with careful design the optimal sequence of an RNA/DNA chimera primer or probe for a specific application will require minimal experimentation.

The disclosed method can be used with any nucleic acid amplification reaction, for singleplex and multiplex reactions and for assays requiring a nucleic acid amplification reaction as a prior step, such as HRM analysis. Forms of nucleic acid amplification for use of the disclosed RNA/DNA chimera include nucleic acid amplification reactions involving exponential amplification, either isothermal or with thermal cycling, nucleic acid amplification reactions requiring exponential amplification, either isothermal or with thermal cycling, nucleic acid amplification reactions involving isothermal linear amplification, nucleic acid amplification reactions requiring isothermal linear amplification, nucleic acid amplification reactions involving rolling circle amplification, nucleic acid amplification reactions involving the polymerase chain reaction, and nucleic acid amplification reactions not involving thermal cycling. Examples of nucleic acid amplification reactions are exponential rolling circle amplification (ERCA) (referred to as strand displacement cascade amplification in PCT Application No. WO 97/19193 and as hyperbranched rolling circle amplification in Lizardi et al., Nature Genetics 19(3):225 232 (1998)) and rolling circle amplification (RCA) (U.S. Pat. No. 5,854,033; PCT Application No. WO 97/19193; Lizardi et al., Nature Genetics 19(3):225 232 (1998)); multiple displacement amplification (MDA) (PCT Application WO 99/18241); strand displacement amplification (SDA) (Walker et al., Nucleic Acids Research 20:1691 1696 (1992), Walker et al., Proc. Natl. Acad. Sci. USA 89:392 396 (1992)); nucleic acid sequence based amplification (NASBA) (Compton, Nature 350:91 92 (1991)); transcription-mediated amplification (TMA) (Nelson, Crit. Rev Clin Lab Sci 35:369 414 (1998)); polymerase chain reaction (PCR), real-time PCR, and other exponential amplification techniques involving thermal cycling, self-sustained sequence replication (3SR), and amplification with Qβ replicase (Birkenmeyer and Mushahwar, J. Virological Methods 35:117 126 (1991); Landegren, Trends Genetics 9:199 202 (1993)); various linear amplification techniques involving thermal cycling such as cycle sequencing (Craxton et al., Methods Companion Methods in Enzymology 3:20 26 (1991)).

Preferred forms of nucleic acid amplification assays for use of the disclosed RNA/DNA chimera include "real-time PCR" assays, also referred to herein as "quantitative PCR (qPCR)", and "high resolution melting (HRM)" analysis. In qPCR methods, the progress of the PCR reaction is monitored as it occurs (i.e., in real time). In such methods, fluorescent dsDNA-binding dyes, (such as SYBR Green I), or dual-labeled probes (such as molecular beacons or Taqman probes) are used to measure the amount of amplified product in real time. The most important difference between the dual labeled probe and the non specific fluorescent dyes is that the non specific fluorescent dye detects all double stranded DNA including non-specific amplification products. On the other hand, dual labeled probe methods have the disadvantage of requiring the synthesis of different probes for different sequences, thus raising assay setup and running costs. In addition, the specific probes do not enable the post PCR analysis such as Tm (melting point) and HRM, which is possible with non specific dyes.

In High Resolution Melting (HRM) assays, a closed-tube, post-PCR method enables the analysis of genetic variations (SNPs, mutations, methylations) in PCR amplicons. It goes beyond the power of classical melting curve analysis by allowing studying the thermal denaturation of a double-stranded DNA in much more detail and with much higher information yield than ever before. HRM characterizes nucleic acid samples based on their disassociation (melting) behavior. Samples can be discriminated according to their sequence, length, GC content or strand complementarity. Even single base changes such as SNPs (single nucleotide polymorphisms) can be readily identified.

The most important High Resolution Melting application is gene scanning—the search for the presence of unknown variations in PCR amplicons prior to or as an alternative to sequencing. Mutations in PCR products are detectable by High Resolution Melting because they change the shape of DNA melting curves. A combination of new-generation DNA dyes, high-end instrumentation and sophisticated analysis software allows to detect these changes and to derive information about the underlying sequence constellation.

Kits

The present invention also provides kits, typically multi-container units comprising components useful for practicing the present method. In some embodiments a kit contains a primer or a set of primers at least one of which is an RNA/DNA chimera as disclosed herein. Other components of the kit include the reagents and enzymes necessary to carry out the amplification reaction, for example, the substrate nucleoside triphosphates, divalent cations, reaction buffer, appropriate DNA polymerase, protocols, and instructions for carrying out the reaction.

The kits can be used for any application which involves a nucleic acid amplification reaction, such as diagnostic kits for infectious agents, kits for prenatal diagnosis of chromosomal abnormalities, kits for diagnosis of genetic diseases, kits for sex determination, etc.

In some embodiments the kit further comprises the means to detect the products of the amplification reaction. A variety of options are available for measuring the amplification products as they are formed. One method utilizes labels, such as dyes, which only bind to double stranded DNA. In this type of approach, amplification product (which is double stranded) binds dye molecules in solution to form a complex. With the appropriate dyes, it is possible to distinguish between dye molecules free in solution and dye molecules bound to amplification product. For example, certain dyes fluoresce only when bound to amplification product. Examples of dyes which can be used in methods of this general type include, but are not limited to, Syber Green™ and Pico Green™ from Molecular Probes, Inc., LCGreen from Idaho technology, ethidium bromide, propidium iodide, chromomycin, acridine orange, Hoechst 33258, Toto-1, Yoyo-1, DAPI (4',6-diamidino-2-phenylindole hydrochloride).

In addition, measurement and detection of amplification products may also be made, for example, by monitoring radioactivity, colorimetry, absorption, Fluorescence Resonance Energy Transfer (FRET), magnetic parameters, or enzymatic activity. Thus, labels for the primers and/or probes, which can be employed include, but are not limited to, fluorophores, chromophores, radioactive isotopes, electron dense reagents, enzymes, and ligands having specific binding partners (e.g., biotin-avidin).

Synthesis of RNA/DNA Chimeric Primers

Synthesis of the RNA/DNA chimeric primers is carried out using standard chemical means well known in the art, for example, the diethylphosphoramidite method of Beaucage et al., 1981, Tetrahedron Lett. 22:1859-1862; and the solid support method of U.S. Pat. No. 4,458,066. Preferably, the synthesis reaction is carried out in a commercially available automatic DNA synthesizer using commercially available nucleotide phosphoramidites. Nucleotide phosphoramidites and supports suitable for synthesizing oligonucleotides containing modified nucleotides as used herein are commercially available. RNA/DNA chimeric oligonucleotide synthesis is carried out by the stepwise addition of deoxynucleoside and ribonucleoside monomers to a growing chain. Each addition involves the coupling of a reactive 3' phosphorous group of a nucleoside monomer to the 5' hydroxyl of another nucleoside bound to a solid support. After addition of the final nucleoside, the oligonucleotide is cleaved from the support, protecting groups are removed from the bases, and the RNA/DNA chimeric oligonucleotide is purified for use.

Efficiency

While not wishing to be bound by any theory or any particular mechanism, it is believed that the efficiency of initiation of DNA synthesis in a DNA-dependent DNA polymerase amplification reaction is hampered when RNA is embedded in the initiation zone, whereas the efficiency of the DNA elongation is less strongly affected when RNA is embedded in the template sequence.

However, when undesirable non-template hybridization such as RNA/DNA chimera primer dimer occurs, the initiation zone includes RNA bases. Again, without wishing to be bound by any theory or any particular mechanism, it is assumed that this causes the amplification cycles to be kinetically and/or thermodynamically inefficient. Incorporation of RNA bases into DNA primers probably destabilizes base-pairing. However, the destabilization of the primer dimers is probably more profound than destabilization of the primer-target DNA hybrid. Nakano et al. investigated the thermodynamics of chimeric junctions to DNA and showed that the nearest neighbor $\Delta G_{37° C.}$ of chimeric junctions (rd/dd and dr/dd) was different from DNA hybrids (dd/dd) (Nakano et al. (2004) J Am Chem Soc, 126, 1088-1095). It was not always increased but occurred more frequently.

Thus, using RNA/DNA chimeric primers reduces the primer-dimer artifacts in low template DNA-amplification reactions resulting in increased detection sensitivity in any DNA dependent DNA-polymerization reaction.

This is illustrated in more detail in the following example, using a hypothetical target sequence. Referring to FIG. 1, the sequence set forth in the template target SEQ ID NO:1 is to be amplified with RNA/DNA chimera primers (forward primer: SEQ ID NO:2; reverse primer: SEQ ID NO:3). In the first amplification cycle, initiation and synthesis of the entire length of the amplicon involves using only DNA bases as a template.

Figure 2:
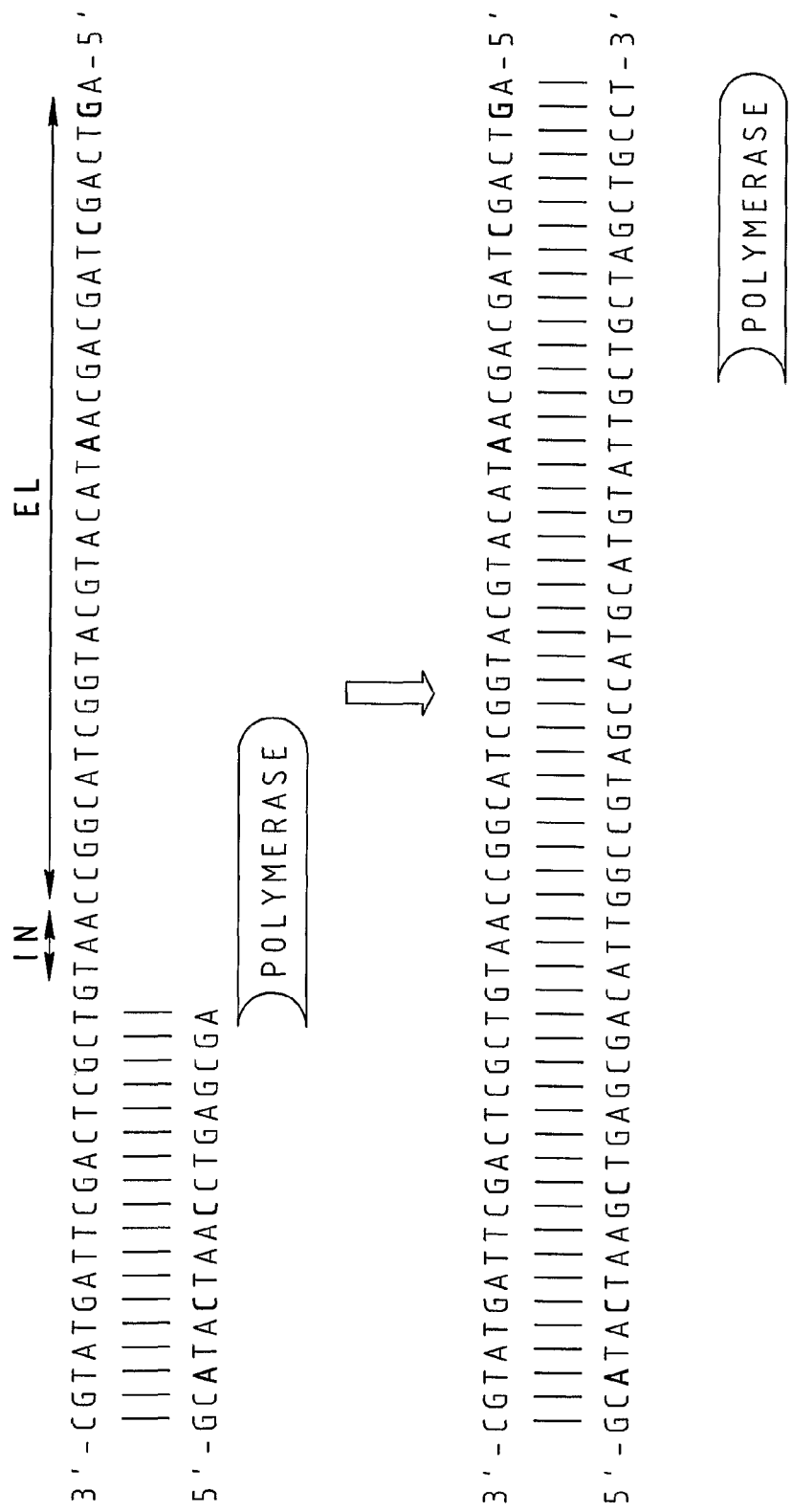
FIG. 2 is a diagram showing how the second cycle of a template dependent amplification using RNA/DNA chimeric primers proceeds. The elongation zone (EL) contains RNA bases. RNA bases are bolded.
Figure 3:
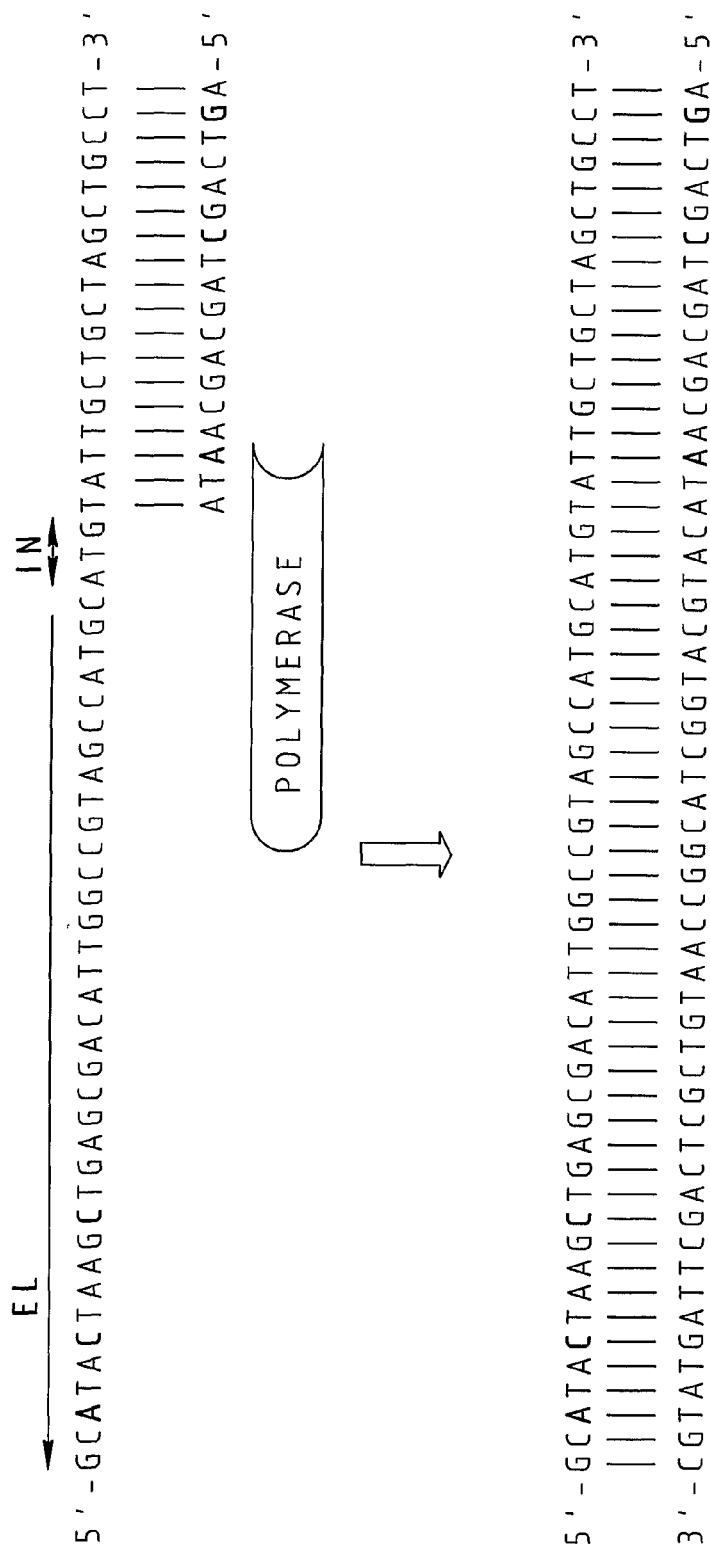
FIG. 3 is a diagram showing how the third cycle of a template dependent amplification using RNA/DNA chimeric primers proceeds. The elongation zone (EL) contains RNA bases. RNA bases are bolded.

Referring now to FIG. 2 and FIG. 3, it can be seen that after melting and annealing, the second and third amplification cycle are less efficient since the RNA-embedded primers are now part of the elongation zone, yet feasible. In template-dependent amplification the RNA bases are always located only in the elongation zone.

Figure 4:
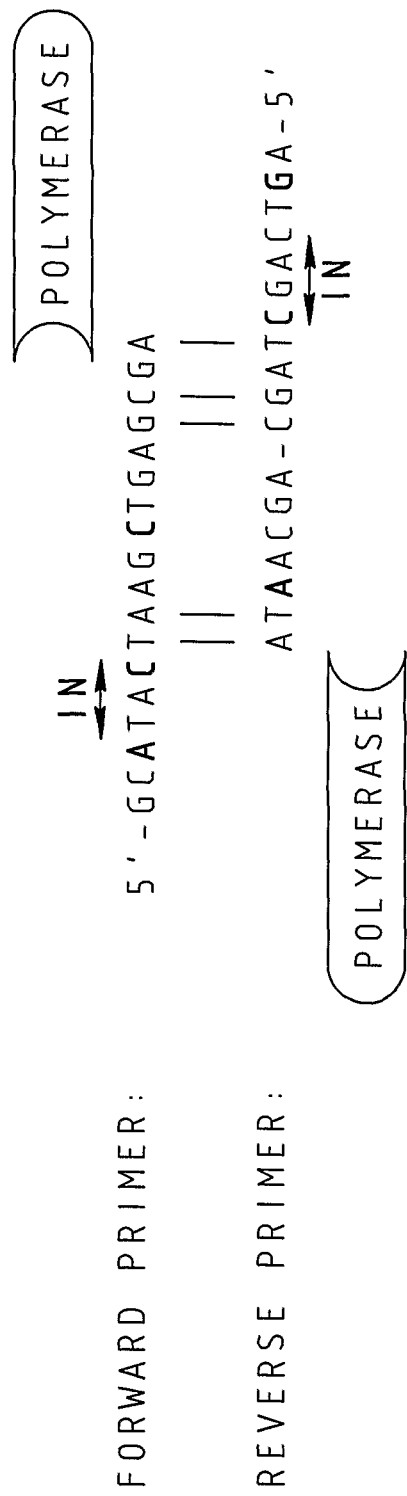
FIG. 4 is a diagram showing how initiation of DNA synthesis is blocked in an RNA/DNA chimeric primer dimer. The initiation of DNA synthesis is inefficient or impossible because the initiation zone (IN) on both strands contains an RNA base. Embedded RNA bases are bolded.

On the other hand, when undesired non-template hybridization occurs, such as in the RNA/DNA chimera primer dimer in FIG. 4, the initiation zone includes RNA bases. This will cause the first amplification cycle and all following cycles to be inefficient. Thus, using RNA/DNA chimera primers reduces the primer-dimer artifacts in low template DNA-amplification reactions and results in increased detection sensitivity in any DNA dependent DNA-polymerization reaction.

The present invention presents evidence of the beneficial effects of RNA/DNA chimera primers on reduction of undesired non-specific amplification products in a DNA dependent DNA polymerase amplification reaction. The findings indicate that RNA/DNA chimera primers eliminated non-specific amplification products and increased the sensitivity and capacity for detection of low concentrations of gene copies in real-time PCR assays.

The present invention will now be illustrated by the following examples, which are intended to be construed in a non-limitative fashion.

EXAMPLES

Methods

Standard oligonucleotides and RNA/DNA chimeric oligonucleotides were synthesized by Integrated DNA Technologies, Inc. (USA), using standard phosphoramidite chemistry using IDT's proprietary synthesis platform. Primer design for the RNA/DNA chimeric oligonucleotide qPCR assay was performed by the SinglePlexer™ software (GenAphora Ltd). Several single RNA bases were embedded in each primer. Twenty μl reactions included 0.5 μM of each primer, $10^4$ plasmid DNA and 10 μl of DyNAmo™ Flash SYBR® Green qPCR Kit (Finnzymes Oy). The amplification cycles were: 95° C., 7 min (first cycle); 94° C., 10 s; 61° C., 30 s; read plate; 76° C., 1 s; read plate; for 39 cycles; followed by 61° C., 1 min; and melting temperature analysis from 65° C.-95° C.

Assays were performed using the 16s RNA gene of bacterial strain *Ehrlichia canis* (EC) and the hsp70 gene of bacterial strain *Babesia canis* (BC) and *Canis* actin pre cloned into pGMT easy (Promega). Real-time qPCR was performed with duplicate samples in different dilution from ~1 to ~$10^6$ copies/µl using Chromo4 (Bio Rad). The ΔC(t) values were calculated as the difference between the C(t) of the sample and the C(t) of the non template control.

Example 1

Real time PCR was performed on $10^4$ copies of the 16S RNA gene of bacterial strain *Ehrlichia canis* (EC) with DNA primers and with RNA/DNA chimeric primers.

DNA Primers:

```
Forward primer:
5'-TCGCTATTAGATGAGCCTACGT-3'      (SEQ ID NO: 4)

Reverse primer:
5'-GAGTCTGGACCGTATCTCAGTT-3'      (SEQ ID NO: 5)
```

RNA/DNA Chimeric Primers (embedded RNA bases are bolded):

```
Forward primer:
5'-TCGCUAUUAGATGAGCCUACGT-3'      (SEQ ID NO: 6)

Reverse primer:
5'-GAGTCTGGACCGUATCTCAGTT-3'      (SEQ ID NO: 7)
```

Figure 5:
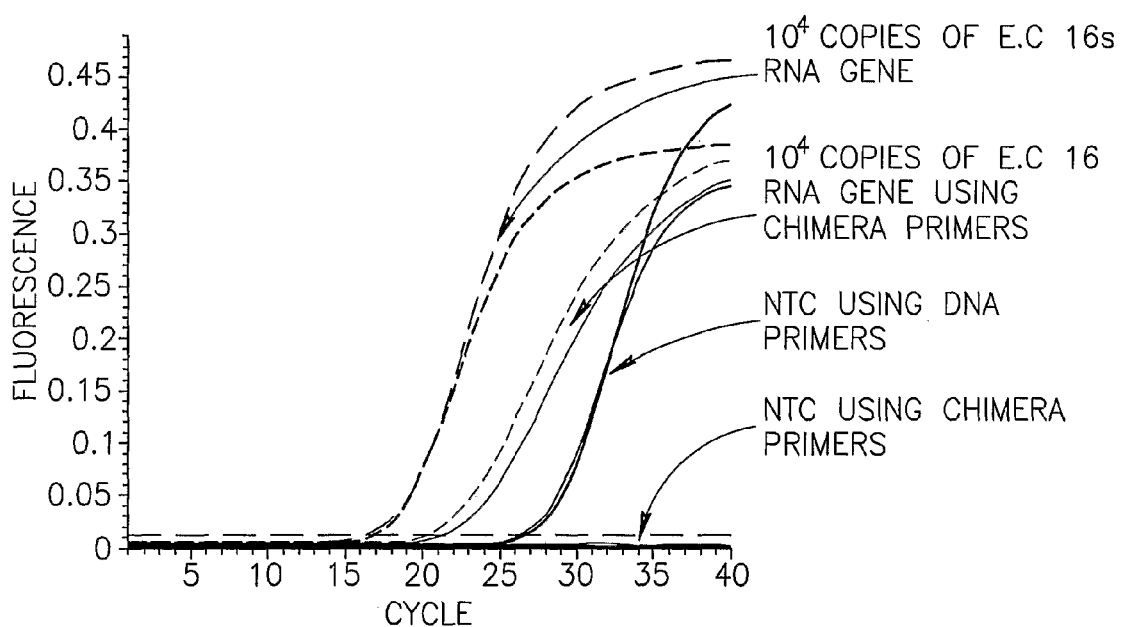
FIG. 5 presents the results of a real-time quantitative PCR assay of the 16s RNA gene of bacterial strain *Ehrlichia canis* (EC) using RNA/DNA chimeric primers and regular DNA primers.

Results are presented in FIG. 5. As can be seen, significant artifacts can be detected in the absence of template (see non-template control (NTC) curve) after cycle 27 when using DNA primers, but remain under the detection threshold when using chimeric primers. Indeed the C(t) values of the specific template dependent products are delayed for approximately 3 cycles but the elimination of non specific products enables prolonging of the detection for at least 13 cycles more than the regular DNA primers reaction.

Figure 6:
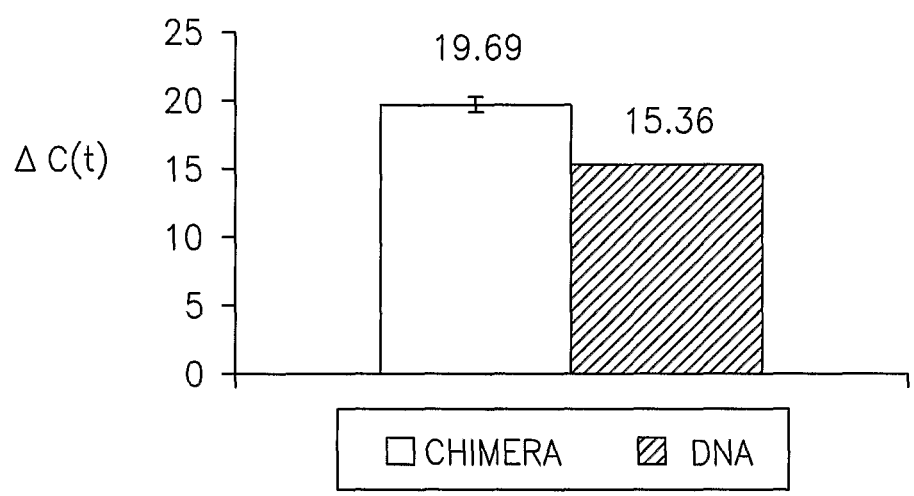
FIG. 6 shows the differences in ΔC(t) values between the detection products of the 16s RNA gene of bacterial strain *Ehrlichia canis* (EC) using RNA/DNA chimeric primers and regular DNA primers. ΔC(t) is calculated here as the difference between C(t) values of the template sample to C(t) values of the Non Target Control (NTC).

This effect of the RNA/DNA chimeric primers is further demonstrated in FIG. 6 which shows the calculated ΔC(t) values of hexaplicate samples. It can be seen that the detection ability of the chimeric primers is more than 4 cycles higher than the regular DNA primers.

Example 2

Figure 7A:
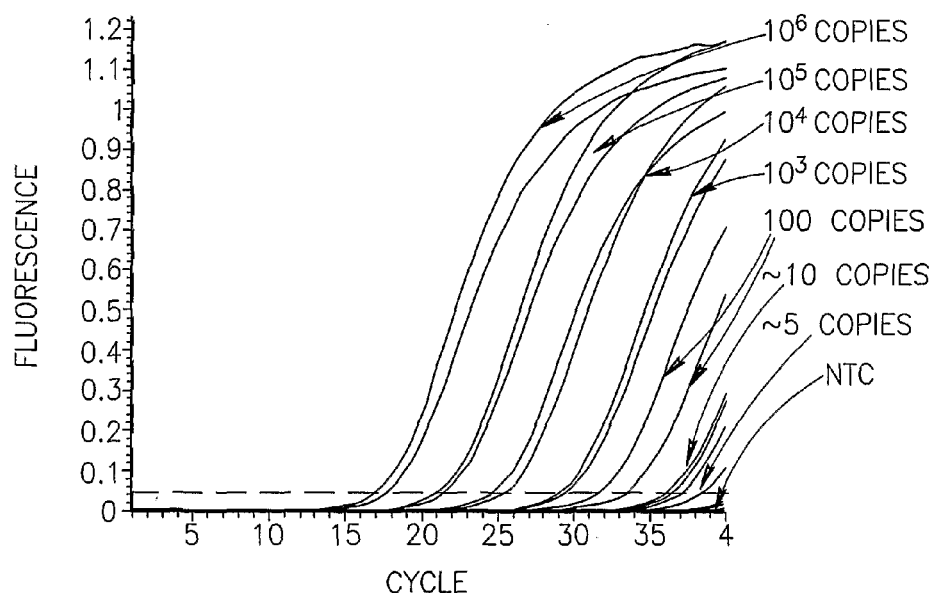
FIG. 7 illustrates the higher sensitivity of a real-time quantitative PCR detection assay of the 16s RNA gene of bacterial strain *Ehrlichia canis* (EC) using RNA/DNA chimeric primers (FIG. 7 A) compared to regular DNA primers (FIG. 7 B).
Figure 7B:
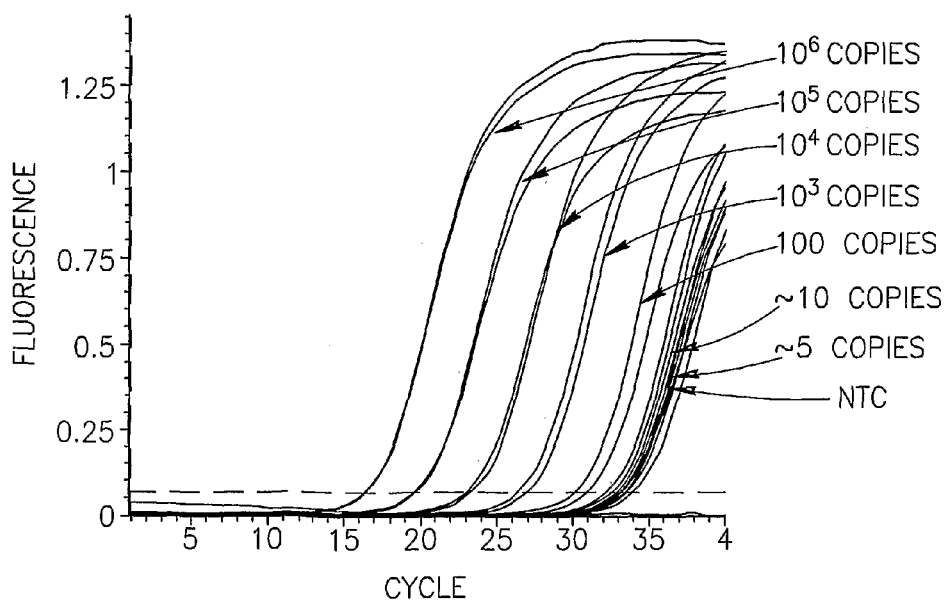
Figure 8A:
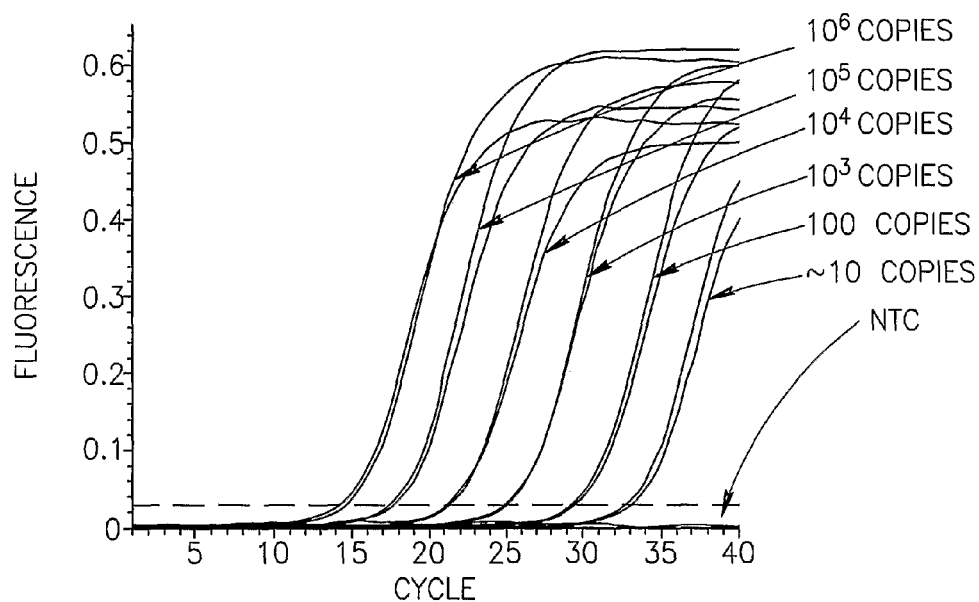
FIG. 8 illustrates the higher sensitivity of a real-time quantitative PCR detection assay of the hsp70 gene of bacterial strain *Babesia canis* (BC) using RNA/DNA chimeric primers (FIG. 8 A) compared to regular DNA primers (FIG. 8 B).
Figure 8B:
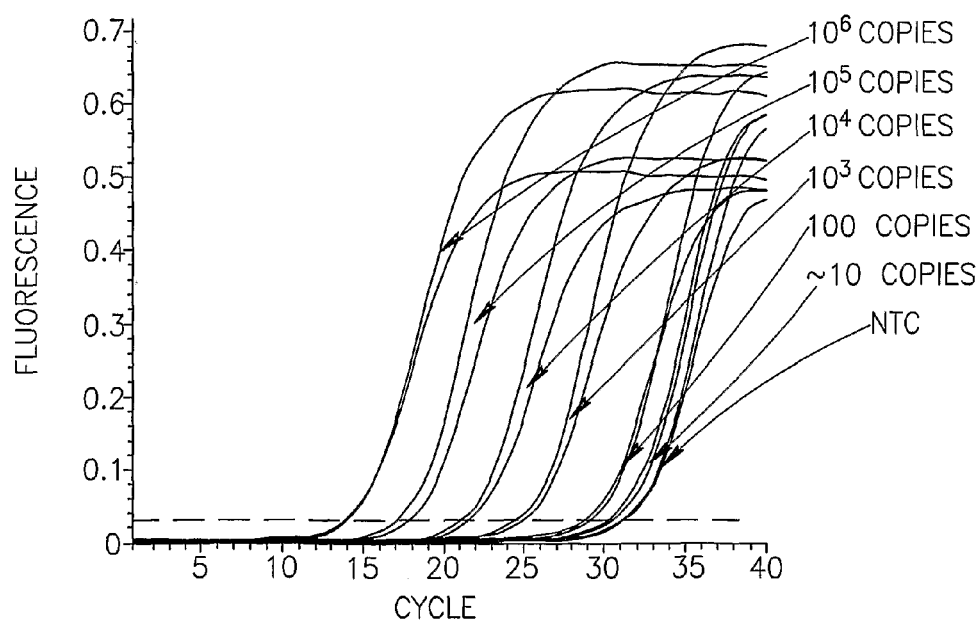

Real time PCR was performed on serial dilutions of the 16S RNA gene of bacterial strain *Ehrlichia canis* (EC) with the same DNA and chimeric primers of example 1. Results are presented in FIGS. 7 A and 7 B. Another Real time PCR, whose results are presented in FIGS. 8 A and 8 B, was performed on serial dilutions of the hsp70 gene of bacterial strain *Babesia canis* (BC) with the following primers.

DNA Primers:

```
Forward primer:
5'-GTCATCACTGTGCCTGCGTACT-3'      (SEQ ID NO: 8)

Reverse primer:
5'-GCATGACGTTGAGACCGGCAAT-3'      (SEQ ID NO: 9)
```

RNA/DNA Chimeric Primers:
(embedded RNA bases are bolded):

```
Forward primer:
5'-GTCATCACTGTGCCTGCGUACT-3'      (SEQ ID NO: 10)

Reverse primer:
5'-GCATGACGTTGAGACCGGCAAT-3'      (SEQ ID NO: 11)
```

This example demonstrates that the sensitivity of the amplification reaction increases when using RNA/DNA chimeric primers. In both cases using chimeric primers enables the detection of low concentrations of gene copies up to a few single copies per tube.

Example 3

In this example a Tm analysis was carried out following qPCR that was performed with DNA and chimeric primers on serial dilutions of the Canine ACTB gene.

DNA Primers:

```
Forward primer:
5'-GCGCAAGTACTCTGTGTGGAT-3'       (SEQ ID NO: 12)

Reverse primer:
5'-GTCGTACTCCTGCTTGCTGAT-3'       (SEQ ID NO: 13)
```

RNA/DNA Chimeric Primers:
(embedded RNA bases are bolded):

```
Forward primer:
5'-GCGCAAGUACTCTGTGTGGAT-3'       (SEQ ID NO: 14)

Reverse primer:
5'-GTCGUACTCCTGCTTGCTGAT-3'       (SEQ ID NO: 15)
```

Figure 9A:
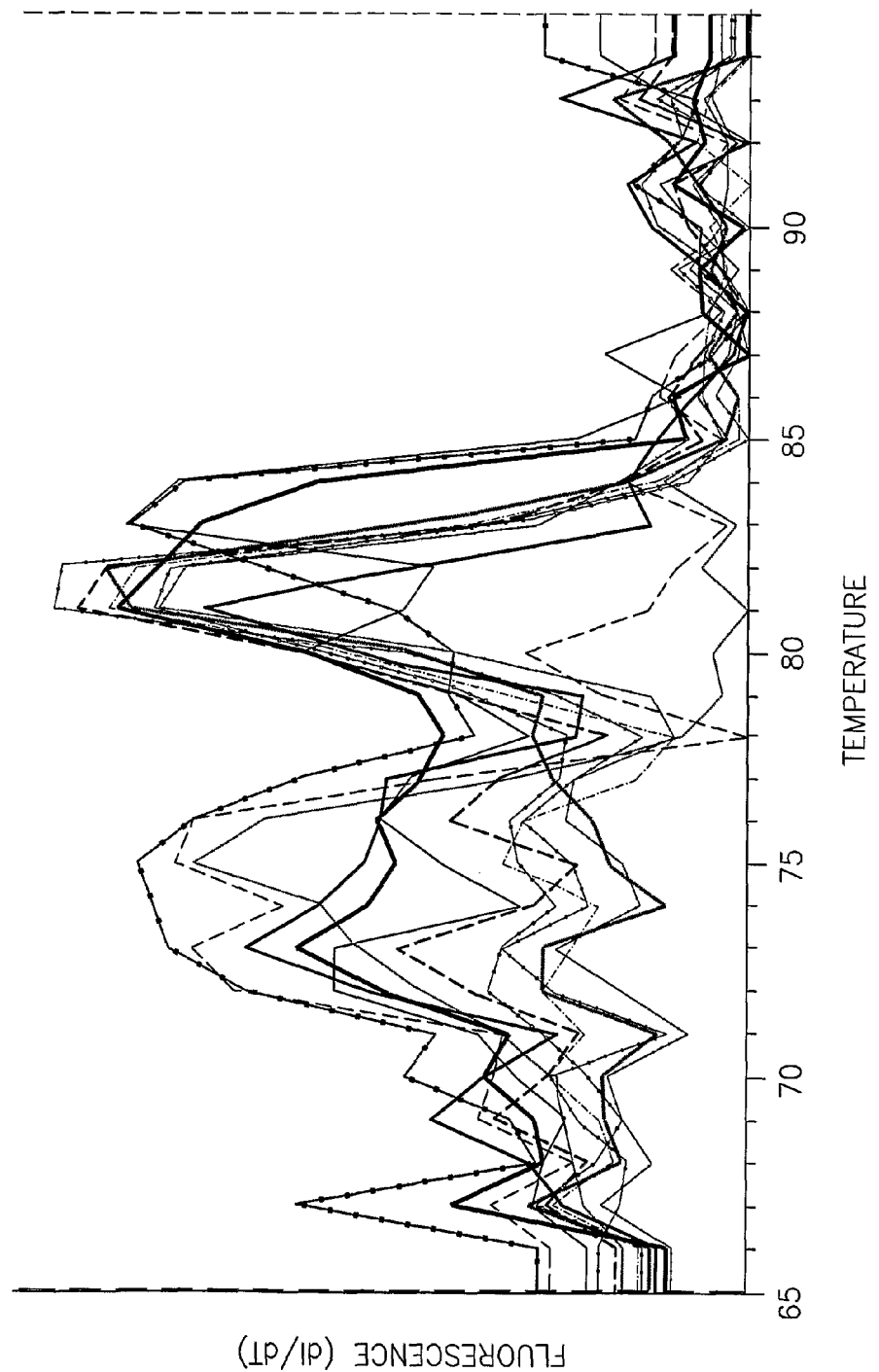
FIG. 9A demonstrated peaks of non specific products in high dilutions using DNA primers, while in the case of chimeric primers; the only significant peak was the ACTB peak One significant peak is a prerequisite to a post PCR HRM analysis.
Figure 9B:
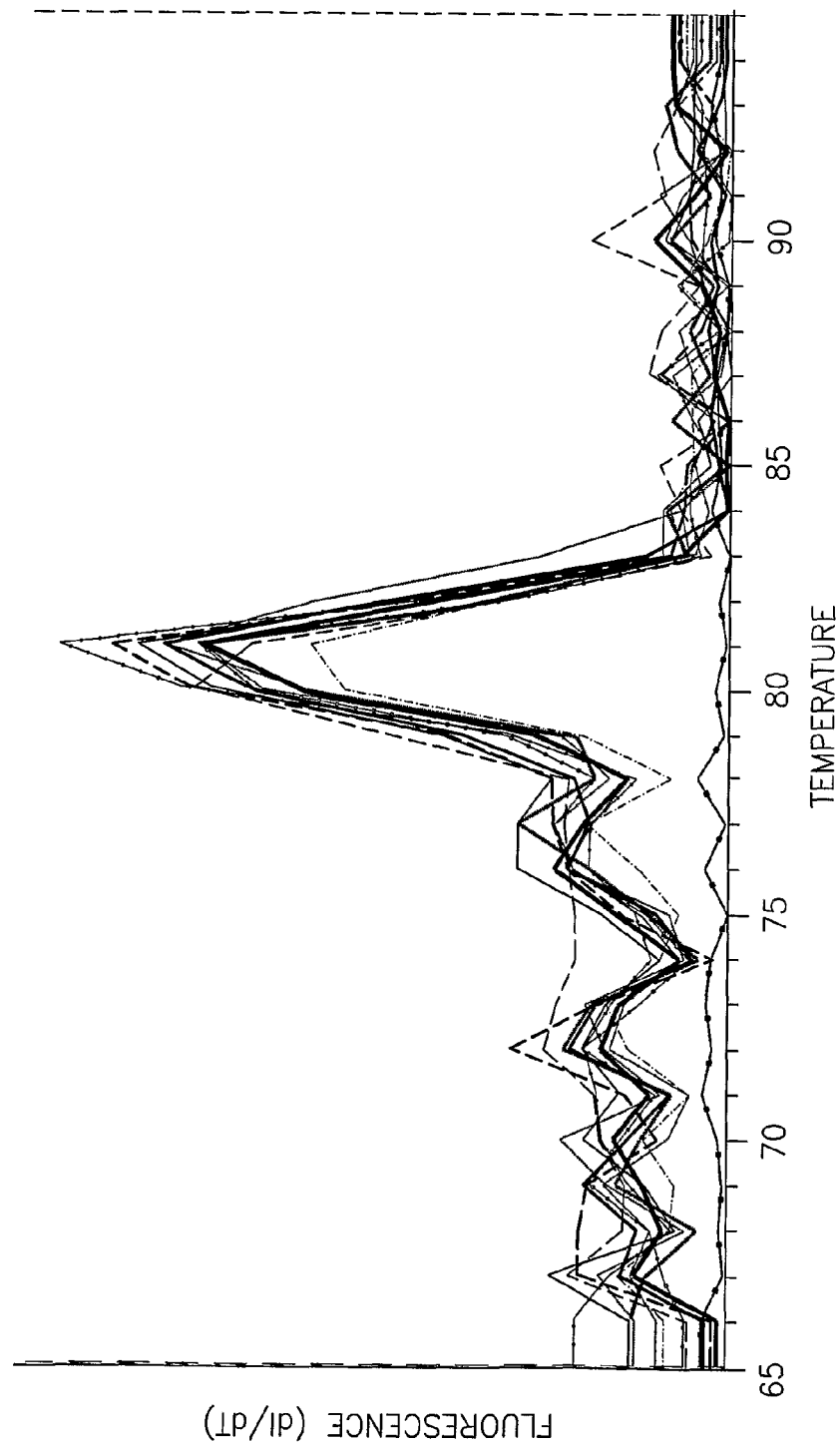
FIG. 9 presents the Tm (melting temperature) analysis using DNA primers (FIG. 9A) and chimeric primers (FIG. 9B) of the *Canis* ACTB gene.

This example demonstrates the increased specificity obtained by using chimeric primers for PCR preceding HRM analysis in low template concentrations. When using DNA primers (FIG. 9A) peaks of non-specific products can be seen in the Tm plot in the range from 70° C. to 78° C., while the Tm peaks of the expected amplicons in high concentration of template range from 81° C. to 82° C. FIG. 9B shows the Tm plot obtained when using DNA/RNA chimeric primers. Here one can see only the expected peaks at low as well as at high concentrations. The Tm plot obtained by using DNA/RNA chimeric primers enables the post PCR HRM analysis in low concentrations as well.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

REFERENCES

1. Rychlik, W. (1995) Mol. Biotechnol. 3, 129-134
2. Watson, R. (1989) Amplifications, 5-6
3. Ferrie, R. M., Schwarz, M. J., Robertson, N. H., Vaudin, S., Super, M., Malone, G. and Little, S. (1992) Am. J. Hum. Genet. 51, 251-262
4. Don, R. H., Cox, P. T., Wainwright, B. J., Baker, K. and Mattick, J. S. (1991) Nucleic Acids Res. 19, 4008
5. Chou, Q., Russell, M., Birch, D. E., Raymond, J. and Bloch, W. (1992) Nucleic Acids Res. 20, 1717-1723

6. D'Aquila, R. T., Bechtel, L. J., Videler, J. A., Eron, J. J., Gocczyca, P. and Kaplan, J. C. (1991) Nucleic Acids Res. 19, 3749
7. TaqMan PCR Reagent Kit Protocol: Part Number 402823, Revision A, May 1996 page 18: P. E. Applied Biosystems
8. Tyagi, S, and Kramer, F. R. (1996) Nature Biotechnology 14:303-308
9. Tyagi, S. et al. (1998) Nat. Biotechnol. 16:49-53
10. Lizardi et al. (1998) Nature Genetics 19(3):225-232
11. Walker et al. (1992) Nucleic Acids Research 20:1691-1696
12. Walker et al. (1992) Proc. Natl. Acad. Sci. USA 89:392-396
13. Compton (1991) Nature 350:91-92
14. Nelson (1998) Crit. Rev Clin Lab Sci 35:369-414
15. Birkenmeyer and Mushahwar (1991) J. Virological Methods 35:117-126
16. Landegren (1993) Trends Genetics 9:199-202
17. Craxton et al. (1991) Methods Companion Methods in Enzymology 3:20-26
18. Beaucage et al. (1981) Tetrahedron Lett. 22:1859-1862
19. Nakano, S., Kanzaki, T. and Sugimoto, N. (2004) J. Am. Chem. Soc. 126, 1088-1095

The invention claimed is:

1. A method of reducing or eliminating formation of artifacts and non-specific amplification products in a DNA-dependent DNA polymerase amplification reaction, the method comprising:
   conducting a nucleic acid amplification reaction using at least one RNA/DNA chimeric oligonucleotide as a forward or as a reverse primer or as a probe, and using a DNA-dependent DNA polymerase;
   wherein the chimeric oligonucleotide comprises at least one ribonucleotide located within 10 nucleotides adjacent to the 3' end of the chimeric oligonucleotide;
   wherein the at least one ribonucleotide impedes DNA synthesis from primer-primer dimers or primer-probe dimers; and
   wherein no two ribonucleotides in the chimeric oligonucleotide are adjacent to one another.

2. The method of claim 1 wherein the forward primer and the reverse primer are both RNA/DNA chimeric oligonucleotides.

3. The method of claim 1 wherein all the primers and probes used in the amplification reaction have an identical base as the 3' terminal base.

4. The method of claim 3 wherein the identical 3' terminal base of the chimeric oligonucleotides is selected from A or T.

5. The method of claim 1 wherein said at least one ribonucleotide is a base that is adjacent to a complementary base to said 3' end of at least one chimeric oligonucleotide.

6. The method of claim 1 wherein said at least one ribonucleotide in each chimeric oligonucleotide is located within one to 5 nucleotides upstream to at least one of the nucleotides that is complementary to its own 3' end or the 3' end of another primer or probe in the reaction mixture.

7. The method of claim 6 wherein said at least one ribonucleotide in each chimeric oligonucleotide is adjacent to at least one of the nucleotides that is complementary to its own 3' end or the 3' end of another primer or probe in the reaction mixture.

8. The method of claim 1 wherein the DNA-dependent DNA polymerase amplification reaction is selected from the group consisting of: exponential rolling circle amplification (ERCA), rolling circle amplification (RCA), multiple displacement amplification (MDA), strand displacement amplification (SDA), nucleic acid sequence based amplification (NASBA), transcription-mediated amplification (TMA), polymerase chain reaction (PCR), real-time quantitative PCR (qPCR), self-sustained sequence replication (3SR), amplification with Qβ replicase, and cycle sequencing.

9. The method of claim 8, wherein the DNA-dependent DNA polymerase amplification reaction is a real-time quantitative PCR (qPCR).

10. A kit for carrying out a DNA-dependent DNA polymerase amplification reaction comprising:
   (i) at least one RNA/DNA chimeric oligonucleotide as a forward or as a reverse primer or as a probe;
   wherein the chimeric oligonucleotide comprises at least one ribonucleotide located within 10 nucleotides adjacent to the 3' end of the chimeric oligonucleotide;
   wherein the at least one ribonucleotide impedes DNA synthesis from primer-primer dimers or primer-probe dimers; and
   wherein no two ribonucleotides in the chimeric oligonucleotide are adjacent to one another;

(ii) a DNA-dependent DNA polymerase;

(iii) the necessary reagents and buffers to carry out the amplification reaction.

11. The kit of claim 10 wherein the forward primer and the reverse primer are both RNA/DNA chimeric oligonucleotides.

12. The kit of claim 10 wherein all the primers and probes used in the kit have an identical base as the 3' terminal base.

13. The kit of claim 12 wherein the identical 3' terminal base of the chimeric oligonucleotides is selected from A or T.

14. The kit of claim 10 wherein said at least one ribonucleotide is a base that is adjacent to a complementary base to said 3' end of at least one chimeric oligonucleotide.

15. The kit of claim 10 wherein said at least one ribonucleotide in each chimeric oligonucleotide is located within one to 5 nucleotides upstream to at least one of the nucleotides that is complementary to its own 3' end or the 3' end of another primer or probe in the kit.

16. The kit of claim 15 wherein said at least one ribonucleotide in each chimeric oligonucleotide is adjacent to at least one of the nucleotides that is complementary to its own 3' end or the 3' end of another primer or probe in the kit.

17. The kit of claim 10 wherein the DNA-dependent DNA polymerase amplification reaction is selected from the group consisting of: exponential rolling circle amplification (ERCA), rolling circle amplification (RCA), multiple displacement amplification (MDA), strand displacement amplification (SDA), nucleic acid sequence based amplification (NASBA), transcription-mediated amplification (TMA), polymerase chain reaction (PCR), real-time quantitative PCR (qPCR), self-sustained sequence replication (3SR), amplification with Qβ replicase, and cycle sequencing.

18. The kit of claim 17 wherein the DNA-dependent DNA polymerase amplification reaction is a real-time quantitative PCR (qPCR).

19. The kit according to claim 10 further comprising the means to detect the products of the amplification reaction.

* * * * *